(12) United States Patent
Kostrzewski

(10) Patent No.: US 11,446,031 B2
(45) Date of Patent: Sep. 20, 2022

(54) REPLACEABLE STAPLE CARTRIDGE

(71) Applicant: Covidien LP, Mansfield, MA (US)

(72) Inventor: Stanislaw Kostrzewski, Newton, CT (US)

(73) Assignee: Covidien LP, Mansfield, MA (US)

( * ) Notice: Subject to any disclaimer, the term of this patent is extended or adjusted under 35 U.S.C. 154(b) by 189 days.

(21) Appl. No.: 16/886,062

(22) Filed: May 28, 2020

(65) Prior Publication Data

US 2020/0289117 A1 Sep. 17, 2020

Related U.S. Application Data

(60) Continuation of application No. 15/818,536, filed on Nov. 20, 2017, now Pat. No. 10,695,059, which is a division of application No. 13/106,111, filed on May 12, 2011, now Pat. No. 9,820,741.

(51) Int. Cl.
| | |
|---|---|
| A61B 17/068 | (2006.01) |
| A61B 17/072 | (2006.01) |
| A61B 17/00 | (2006.01) |
| A61B 17/29 | (2006.01) |
| A61B 50/30 | (2016.01) |
| A61B 90/00 | (2016.01) |

(52) U.S. Cl.
CPC .. *A61B 17/07207* (2013.01); *A61B 17/00234* (2013.01); *A61B 50/30* (2016.02); *A61B 2017/00473* (2013.01); *A61B 2017/00477* (2013.01); *A61B 2017/07271* (2013.01); *A61B 2017/2931* (2013.01); *A61B 2090/0814* (2016.02); *Y10T 29/53909* (2015.01)

(58) Field of Classification Search
CPC .. A61B 2017/0023; A61B 2017/07271; A61B 2017/07214; A61B 2017/2931

USPC .......................................... 227/175.1–181.1
See application file for complete search history.

(56) References Cited

U.S. PATENT DOCUMENTS

| | | | |
|---|---|---|---|
| 4,568,009 A | 2/1986 | Green | |
| 4,605,001 A | 8/1986 | Rothfuss et al. | |
| 4,633,874 A | 1/1987 | Chow et al. | |
| 4,819,853 A | 4/1989 | Green | |
| 5,275,323 A * | 1/1994 | Schulze | A61B 17/07207 227/176.1 |

(Continued)

FOREIGN PATENT DOCUMENTS

| | | |
|---|---|---|
| EP | 2316348 A1 | 5/2011 |
| EP | 2713900 A1 | 4/2014 |

OTHER PUBLICATIONS

European Search Report for EP 12167634.0 date of completion is Oct. 19, 2012 (10 pages).

(Continued)

*Primary Examiner* — Eyamindae C Jallow
(74) *Attorney, Agent, or Firm* — Carter, DeLuca & Farrell LLP

(57) ABSTRACT

A stapling device including a replaceable loading unit is provided. The loading unit includes an elongated body and a stapling assembly having a first jaw and a second jaw. The first jaw of the stapling assembly includes an anvil assembly. The second jaw of the stapling assembly includes a releasably mounted cartridge assembly having a detent connection with the stapling assembly. Also provided is a tool for removing facilitating the separation of a replaceable cartridge assembly from a loading unit.

20 Claims, 17 Drawing Sheets

(56) References Cited

U.S. PATENT DOCUMENTS

| | | | |
|---|---|---|---|
| 5,356,064 A | 10/1994 | Green et al. | |
| 5,415,335 A | 5/1995 | Knodell, Jr. | |
| 5,439,155 A | 8/1995 | Viola | |
| 5,462,215 A | 10/1995 | Viola et al. | |
| 5,529,235 A * | 6/1996 | Boiarski | A61B 90/98 600/101 |
| 5,582,611 A | 12/1996 | Tsuruta et al. | |
| 5,632,432 A | 5/1997 | Schulze et al. | |
| 5,634,582 A | 6/1997 | Morrison, Jr. et al. | |
| 5,673,842 A | 10/1997 | Bittner et al. | |
| 5,752,644 A | 5/1998 | Bolanos et al. | |
| 5,762,256 A | 6/1998 | Mastri et al. | |
| 5,865,361 A * | 2/1999 | Milliman | A61B 17/068 227/176.1 |
| 7,207,472 B2 | 4/2007 | Wukusick et al. | |
| 7,942,303 B2 | 5/2011 | Shah | |
| 7,954,682 B2 * | 6/2011 | Giordano | A61B 17/07207 227/181.1 |
| 7,954,687 B2 | 6/2011 | Zemlok et al. | |
| 8,007,513 B2 | 8/2011 | Nalagatla et al. | |
| 8,015,976 B2 | 9/2011 | Shah | |
| 8,210,416 B2 | 7/2012 | Milliman et al. | |
| 8,231,043 B2 | 7/2012 | Tarinelli et al. | |
| 8,371,492 B2 * | 2/2013 | Aranyi | A61B 17/07292 227/176.1 |
| 9,820,741 B2 | 11/2017 | Kostrzewski | |
| 9,962,161 B2 | 5/2018 | Scheib | |
| 10,695,059 B2 | 6/2020 | Kostrzewski | |
| 2006/0151569 A1 | 7/2006 | Ehrenfels et al. | |
| 2007/0114262 A1 | 5/2007 | Mastri et al. | |
| 2007/0167960 A1 | 7/2007 | Roth et al. | |
| 2008/0017693 A1 | 1/2008 | Mastri et al. | |
| 2008/0083809 A1 | 4/2008 | Scirica | |
| 2008/0083810 A1 * | 4/2008 | Marczyk | A61B 17/07207 227/175.1 |
| 2008/0110960 A1 | 5/2008 | Jankowski | |
| 2008/0127785 A1 | 6/2008 | Sun | |
| 2008/0142565 A1 | 6/2008 | Ehrenfels et al. | |
| 2008/0179374 A1 | 7/2008 | Beardsley | |
| 2008/0308603 A1 | 12/2008 | Shelton et al. | |
| 2008/0314954 A1 | 12/2008 | Boudreaux | |
| 2009/0242610 A1 | 10/2009 | Shelton, IV et al. | |
| 2009/0266868 A1 * | 10/2009 | Wenchell | A61B 17/07207 227/176.1 |
| 2009/0288029 A1 | 11/2009 | Fuller | |
| 2011/0290853 A1 * | 12/2011 | Shelton, IV | A61B 17/064 227/177.1 |
| 2012/0104072 A1 | 5/2012 | Vidal et al. | |
| 2012/0248172 A1 | 10/2012 | Shelton, IV et al. | |
| 2013/0098969 A1 | 4/2013 | Scirica et al. | |

OTHER PUBLICATIONS

Canadian Office Action dated Feb. 15, 2018, issued in CA Application No. 2,773,414.
Canadian Office Action dated Apr. 9, 2021, corresponding to counterpart Canadian Application No. 3,057,664; 3 pages.
Canadian Office Action dated Nov. 9, 2021, corresponding to counterpart Candian Patent Application 3,057,664; 3 pages.

* cited by examiner

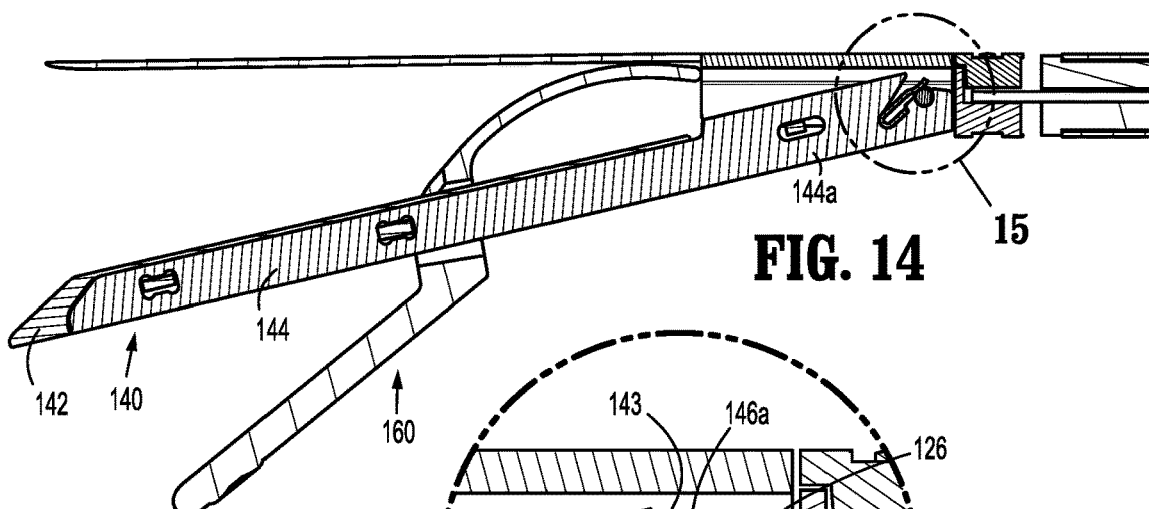
FIG. 14
FIG. 15
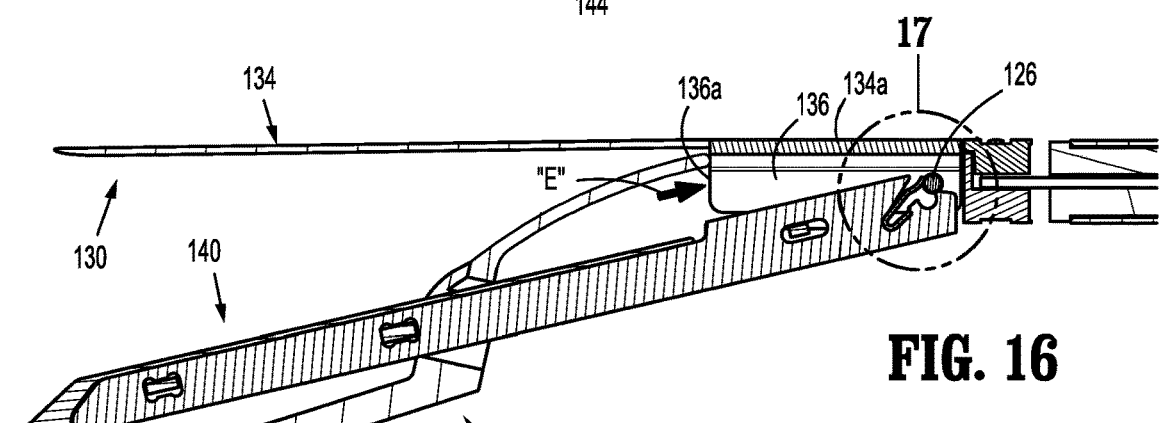
FIG. 16
FIG. 17
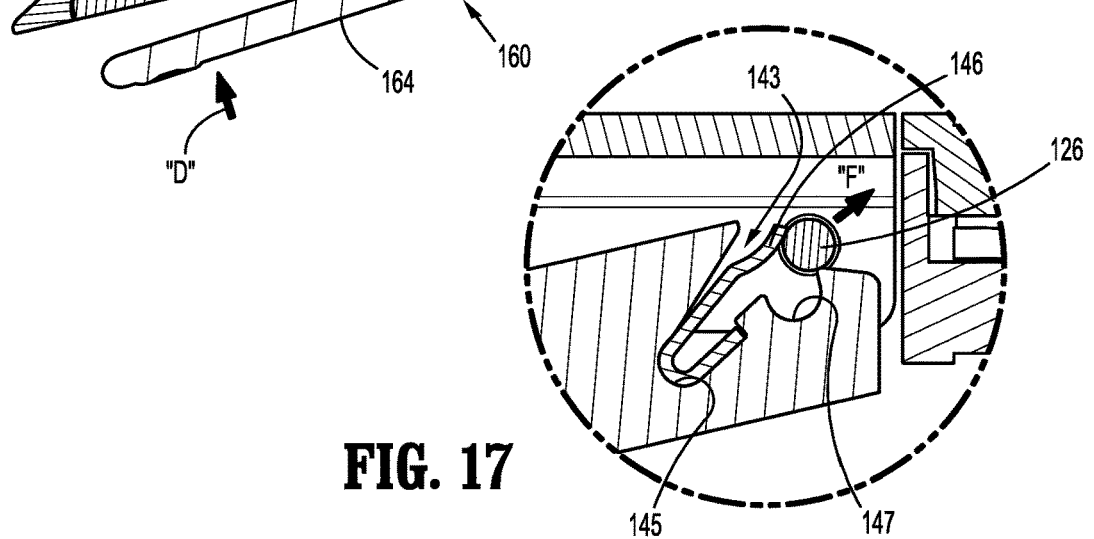

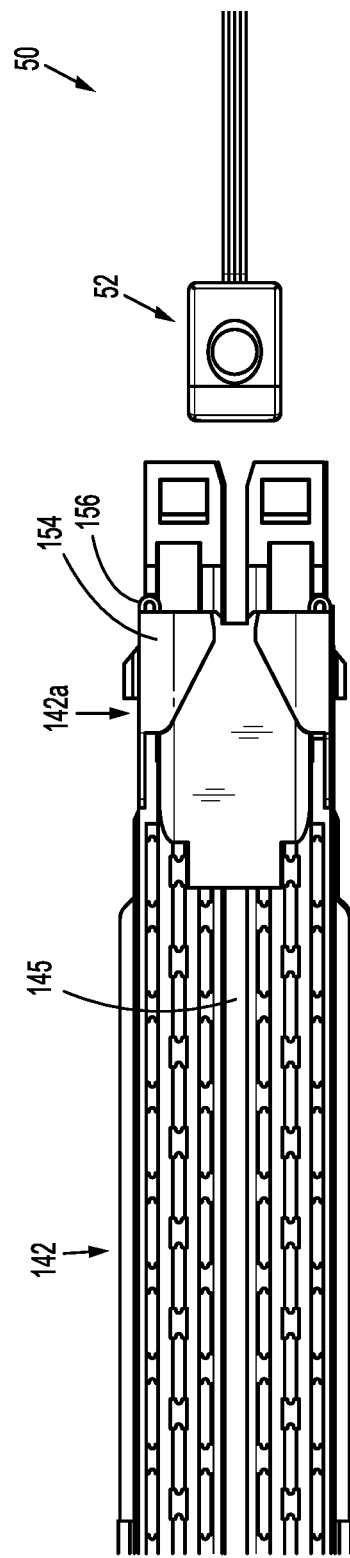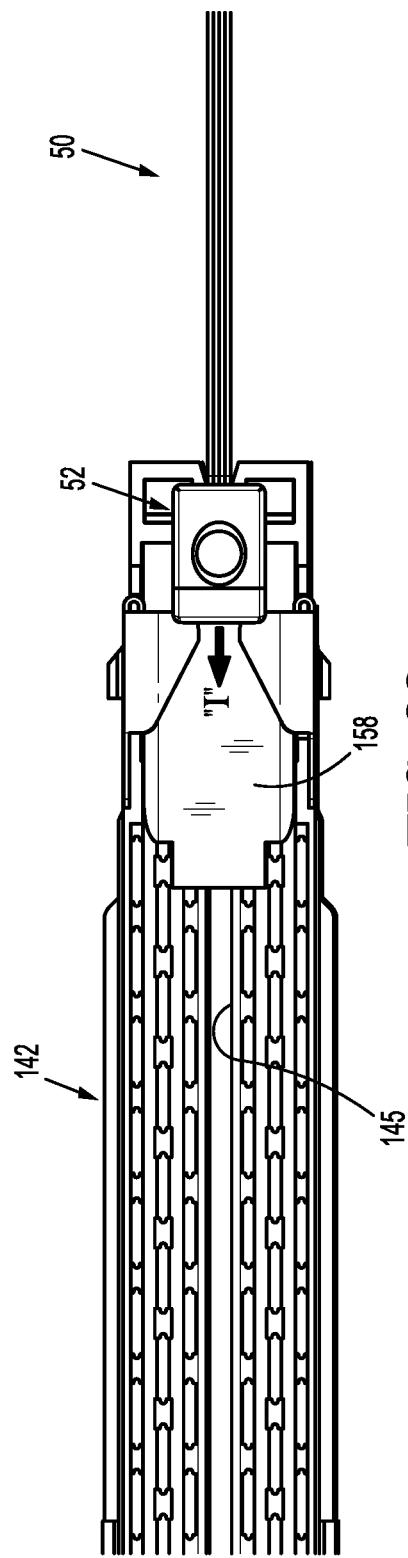

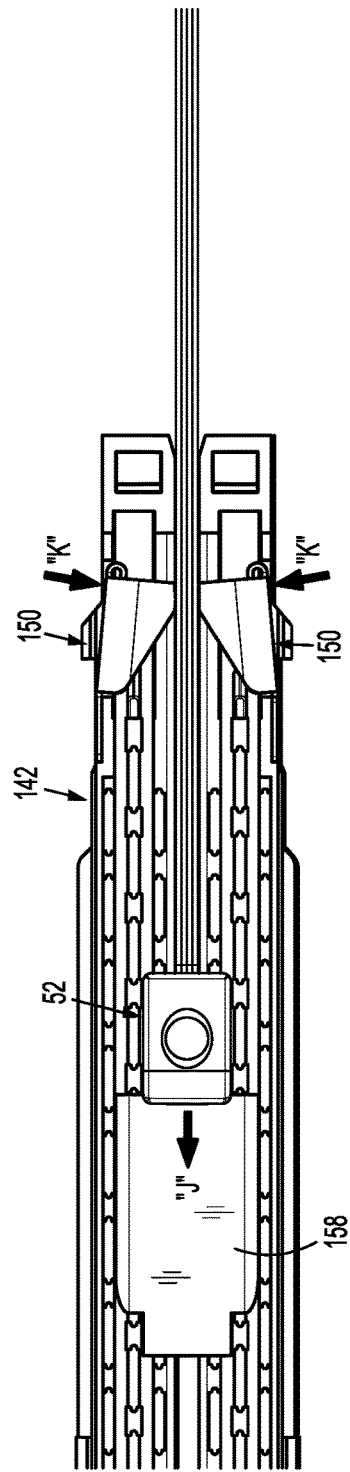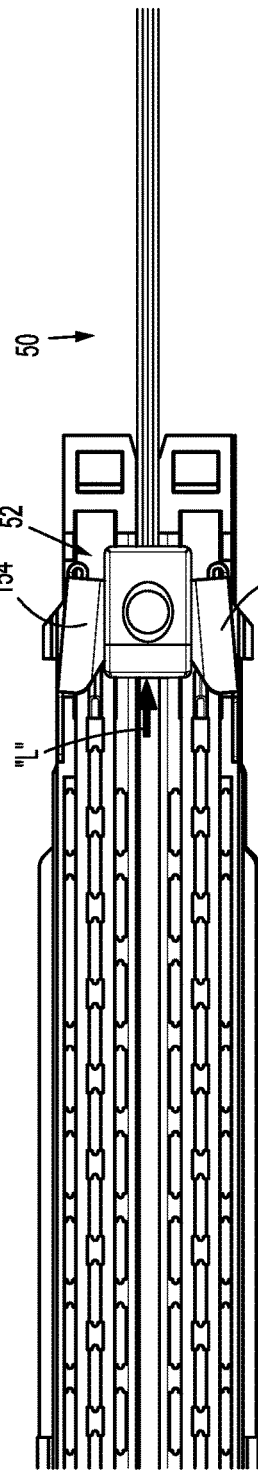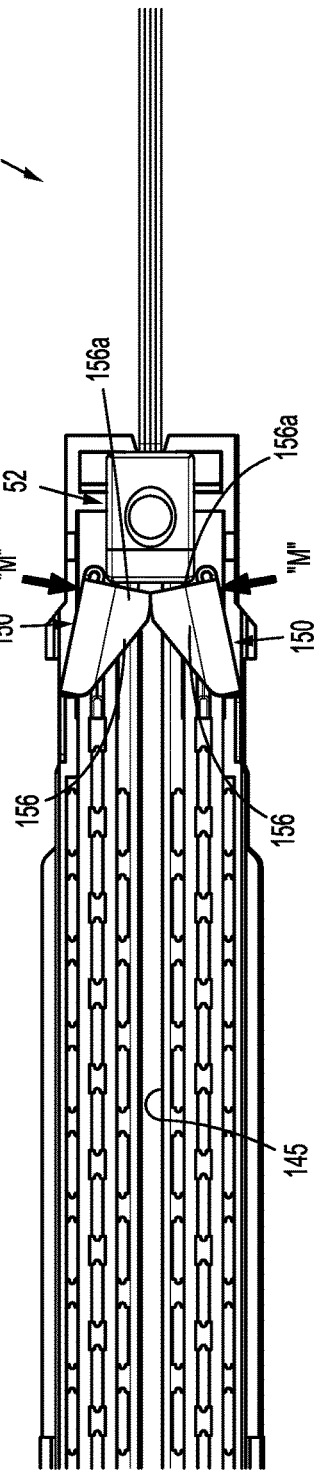

REPLACEABLE STAPLE CARTRIDGE

CROSS-REFERENCE TO RELATED APPLICATIONS

This application is a continuation of U.S. patent application Ser. No. 15/818,536, filed Nov. 20, 2017, which is a divisional of U.S. patent application Ser. No. 13/106,111, filed May 12, 2011, now U.S. Pat. No. 9,820,741. Each of these disclosures is incorporated by reference herein in its entirety.

BACKGROUND

Technical Field

The present disclosure relates to surgical staplers. More particularly, the present disclosure relates to a surgical stapler including a replaceable staple cartridge assembly.

Background of Related Art

Surgical devices for first grasping or clamping tissue between opposing jaw structure and then stapling the tissue with surgical fasteners are well known in the art. In some instruments a knife is provided to cut the tissue which has been stapled by the fasteners. Instruments for this purpose typically include two elongated members, one of which carries a staple cartridge and the other of which includes an anvil. The staple cartridge houses a plurality of staples arranged in at least two lateral rows. The anvil defines a surface for forming the staple legs as the staples are driven from the staple cartridge. Generally, the stapling operation is effected by cam bars that travel longitudinally through the staple cartridge. A knife may travel between the staple rows to longitudinally cut and/or open the stapled tissue between the rows of staples.

Often the stapling assembly of the surgical device is located on a loading unit that is operably connected to a handle assembly. While the handle assembly is configured for multiple uses, the loading unit is configured for a single use. After the single use, the loading unit is removed from the handle assembly and properly disposed. The configuration of the loading units does not permit reloading or replacing of the staple cartridge after the loading unit has been fired.

Therefore, it would be beneficial to have a stapling device that includes a loading unit with a replaceable staple cartridge.

SUMMARY

Accordingly, a stapling device including a replaceable loading unit is provided. The loading unit includes an elongated body and a stapling assembly having a first jaw and a second jaw. The first jaw of the stapling assembly includes an anvil assembly. The second jaw of the stapling assembly includes a releasably mounted cartridge assembly having a detent connection with the stapling assembly. The cartridge assembly may include a carrier having a proximal end configured for selective engagement with the elongated body. The proximal end of the carrier may define a pair of cut-outs. Each of the pair of cut-outs may include a recess and a pivot hole. Each recess may be configured to receive a spring. Each pivot hole may be configured to receive a pivot pin. Each spring may include a flange for selectively retaining a pivot pin within each of the pivot holes.

Also provided is a surgical stapler. The surgical stapler includes an actuation assembly and a stapling assembly operably connected to the actuation assembly. The stapling assembly includes a cartridge assembly removably mounted to the stapling assembly by a detent connection. The stapling assembly may be mounted on a distal end of a loading unit and the loading unit may be removably attached to the actuation assembly.

Also provided is a replaceable cartridge assembly. The cartridge assembly includes a staple cartridge and a carrier configured to receive the staple cartridge. The carrier includes a proximal end configured for selective engagement with a stapling assembly. The carrier may have a resilient spring arranged to form a connection with a stapling assembly. The proximal end of the carrier may define a pair of cut-outs. Each of the pair of cut-outs may include a recess and a pivot hole. Each recess may be configured to receive the spring. Each pivot hole may be configured to receive a pivot pin. Each spring may include a flange for selectively retaining a pivot pin within each of the pivot holes.

Also provided is a tool for separating a replaceable cartridge assembly from a loading unit. The separation tool includes a base portion, a handle portion extending proximally from the base portion, and an engagement portion extending distally from the arcuate portion. The base portion may define an opening configured to receive a proximal end of a cartridge assembly. The tool may further include an arcuate portion extending distally from the base portion. The arcuate portion may be configured to engage an anvil assembly.

Additionally, a surgical stapler is provided. The stapler includes an actuation assembly having an elongate shaft with a distal end. The actuation assembly also includes a flexible drive member that is advanceable in a distal direction. The stapler further includes a stapling assembly having a cartridge assembly with a staple cartridge and an anvil assembly with an anvil member. The stapler also includes an interlocking assembly disposed in the cartridge assembly adjacent the flexible drive member and having at least one interlocking member. The interlocking member has an L-shaped surface and is biased toward the flexible drive member. The L-shaped surface is engaged by the flexible drive member as the flexible drive member is retracted in a proximal direction. The at least one interlocking member is configured to prevent advance of the flexible drive member once the flexible drive member is retracted proximally out of engagement with the at least one interlocking member.

DESCRIPTION OF THE DRAWINGS

Embodiments of a loading unit including a replaceable cartridge assembly are disclosed herein with reference to the drawings, wherein:

FIG. 14 is a cross-sectional side view of the stapling and mounting assemblies of the loading unit of FIG. 12 taken along line 14-14 of FIG. 12;

FIG. 15 is a cross-sectional sectional view of Section 15 of FIG. 14;

FIG. 16 is a cross-sectional side view of the stapling and mounting assemblies of the loading unit of FIG. 14 with the cartridge assembly partially disengaged from the loading unit;

FIG. 17 is a cross-sectional sectional view of Section 17 of FIG. 16;

FIG. 21 is a bottom view of the staple cartridge of FIG. 20 with the knife assembly completely disengaged from the staple cartridge;

FIG. 22 is a bottom view of the staple cartridge of FIG. 20 with the knife assembly partially engaged with the staple cartridge;

FIG. 23 is a bottom view of the staple cartridge of FIG. 20 showing the knife assembly partially advanced through the staple cartridge;

FIG. 24 is a bottom view of the staple cartridge of FIG. 20 showing the knife assembly partially retracted through the staple cartridge;

FIG. 25 is a bottom view of the staple cartridge of FIG. 20 showing the knife assembly retracted through interlocking plates of the staple cartridge;

DETAILED DESCRIPTION

Embodiments of the presently disclosed loading unit with a replaceable staple cartridge will now be described in detail with reference to the drawings wherein like numerals designate identical or corresponding elements in each of the several views. As is common in the art, the term "proximal" refers to that part or component that is closer to the user or operator, i.e. surgeon or physician, while the term "distal" refers to that part or component that is further away from the user. Although the replaceable staple cartridges of the present disclosure will be described as relates to a disposable loading unit for use with a surgical stapler, the presently disclosed replaceable cartridge assembly may be modified for use with surgical stapling devices that do not include a disposable loading unit.

Figure 1:
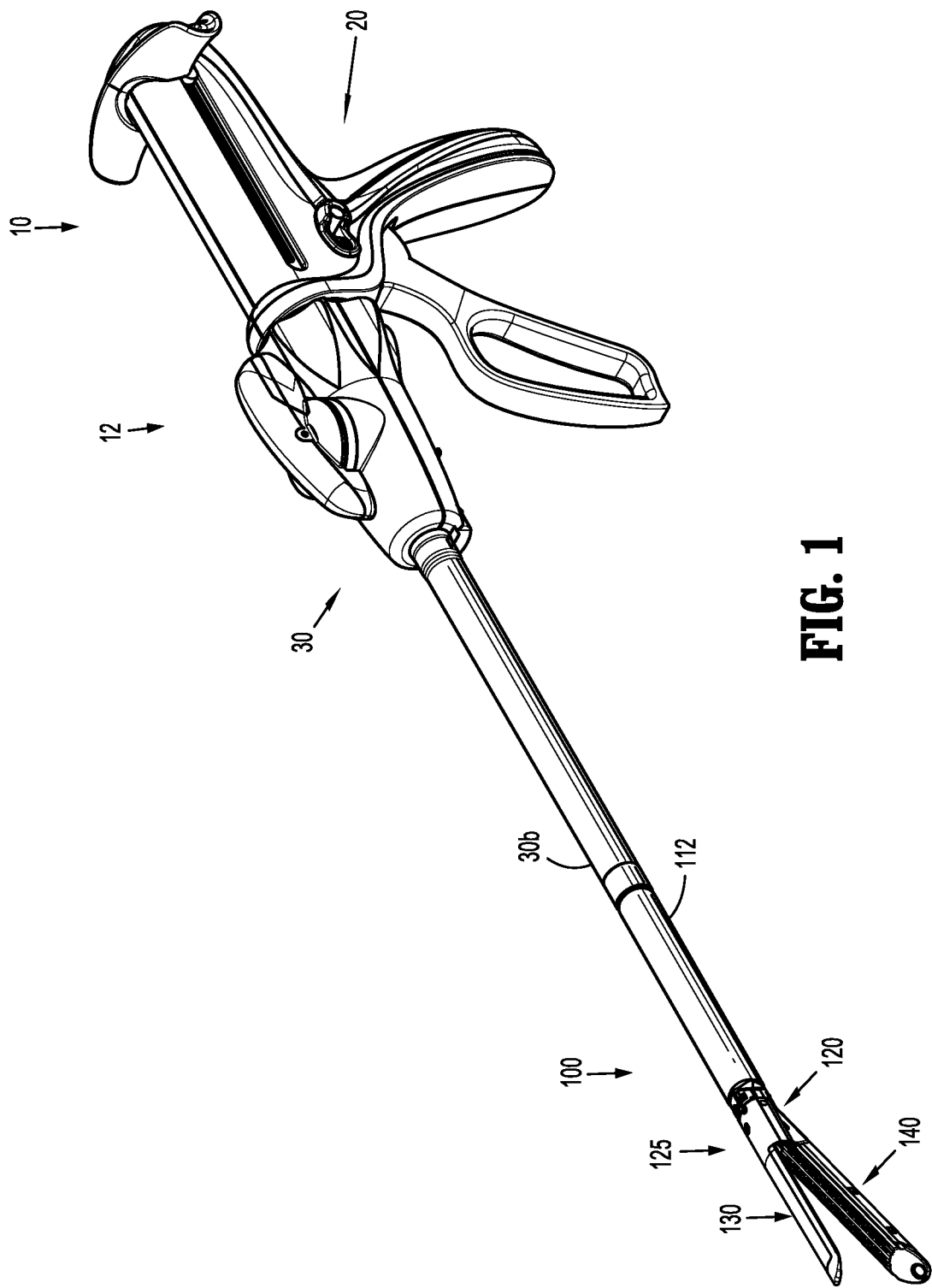
FIG. 1 is a perspective view of a surgical stapler including a loading unit having a replaceable cartridge assembly according to an embodiment of the present disclosure.

FIG. 1 illustrates a surgical stapling device 10 including an embodiment of a disposable loading unit according to the present disclosure shown generally as loading unit 100. As shown in FIG. 1, and as will be discussed hereinbelow, loading unit 100 is configured for attachment to an actuator assembly 12 to form surgical stapler 10. Actuator assembly 12 includes a handle assembly 20 and an elongated body 30 extending from handle assembly 20. As shown, elongated body 30 is configured for use in closed procedures, i.e., laparoscopic, endoscopic, arthroscopic, however, elongated body 30 may be shortened or eliminated for use in open procedures. In the present disclosure, actuator assembly 12 will only be described to the extent necessary to fully disclose loading unit 100. For a more detailed description of the structure and function of a surgical stapler similar to actuator assembly 12, please refer to commonly owed U.S. Pat. No. 5,865,361 to Milliman et al. ("Milliman '361 patent"), the content of which is incorporated herein in by reference in its entirety.

Although the following disclosure will relate to the use of loading unit 100 with actuator assembly 12, loading units constructed in accordance with the present disclosure may be configured for use with actuation assemblies having alternative configurations. For example, loading units may be configured for use with an actuator assembly that is electrically or gas powered and/or includes a pencil grip. It should also be understood that the aspects of the present disclosure may be modified for use with loading units having alternative configurations, and as discussed above, with surgical stapling devices with no loading unit. In other words, the stapling assembly is mounted directly to the actuator assembly.

With reference now to FIGS. 1-5, loading unit 100 includes an elongated body portion 110, a mounting assembly 120 pivotally mounted to elongated body portion 110 and a stapling assembly 125 operably engaged with the mounting assembly 120. Mounting assembly 120 includes upper and lower mounting portions 122, 124. Stapling assembly 125 includes an anvil assembly 130 operably secured to upper and lower mounting portions 122, 124 and a removable cartridge assembly 140. The cartridge assembly 140 is pivotally secured to and releasable from lower mounting portion 124. Stapling assembly 125 configured to capture, staple and cut tissue.

Figure 3:
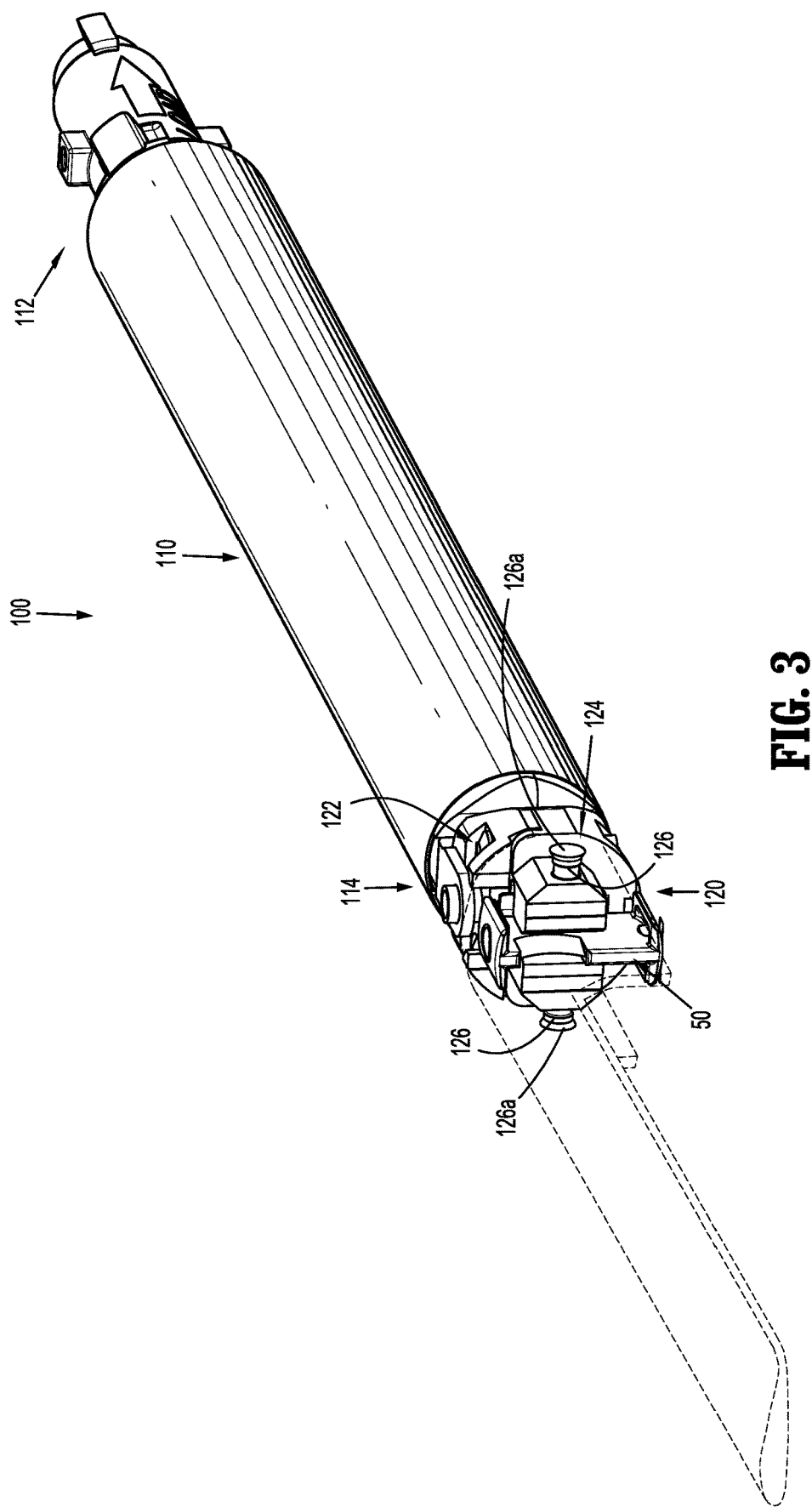
FIG. 3 is an enlarged perspective view of the loading unit of FIGS. 1 and 2 with the anvil portion of the anvil assembly shown in phantom.

With particular reference now to FIG. 3, elongated body portion 110 of loading unit 100 includes a proximal end 112 configured for operable engagement with a distal end 30b (FIG. 1) of elongated body 30 of actuator assembly 12. For a detailed discussion of the attachment of loading unit 100 with actuator assembly 12, please refer to the 361' Milliman patent.

With reference still to FIG. 3, mounting assembly 120 is operably connected to a distal end 114 of elongated body portion 110 of loading unit 100. Mounting assembly 120 includes upper and lower mounting portions 122, 124.

Upper and lower mounting portions 122, 124 are pivotally connected to distal end 114 of elongated body portion 110 and are configured to permit the articulation of stapling assembly 125 relative elongated body portion 110. As will be discussed in further detail below, mounting assembly 120 is configured to receive a flexible drive assembly 50 (FIG. 19) therethrough for actuating stapling assembly 125. For a more detailed discussion of the structure and function of a mounting assembly similar to mounting assembly 120, please refer to the Milliman '361 patent.

Still referring to FIG. 3, lower mounting portion 122 of mounting assembly 120 includes a pair of pivot pins 126. Pivot pins 126 extend laterally outward from lower mounting portion 122 and include head portions 126a. As will be discussed in further detail below, pivot pins 126 are configured for selective engagement by stapling cartridge 140. Head portions 126a of pivot pins 126 may be configured for selective engagement by anvil assembly 130.

Figure 2:
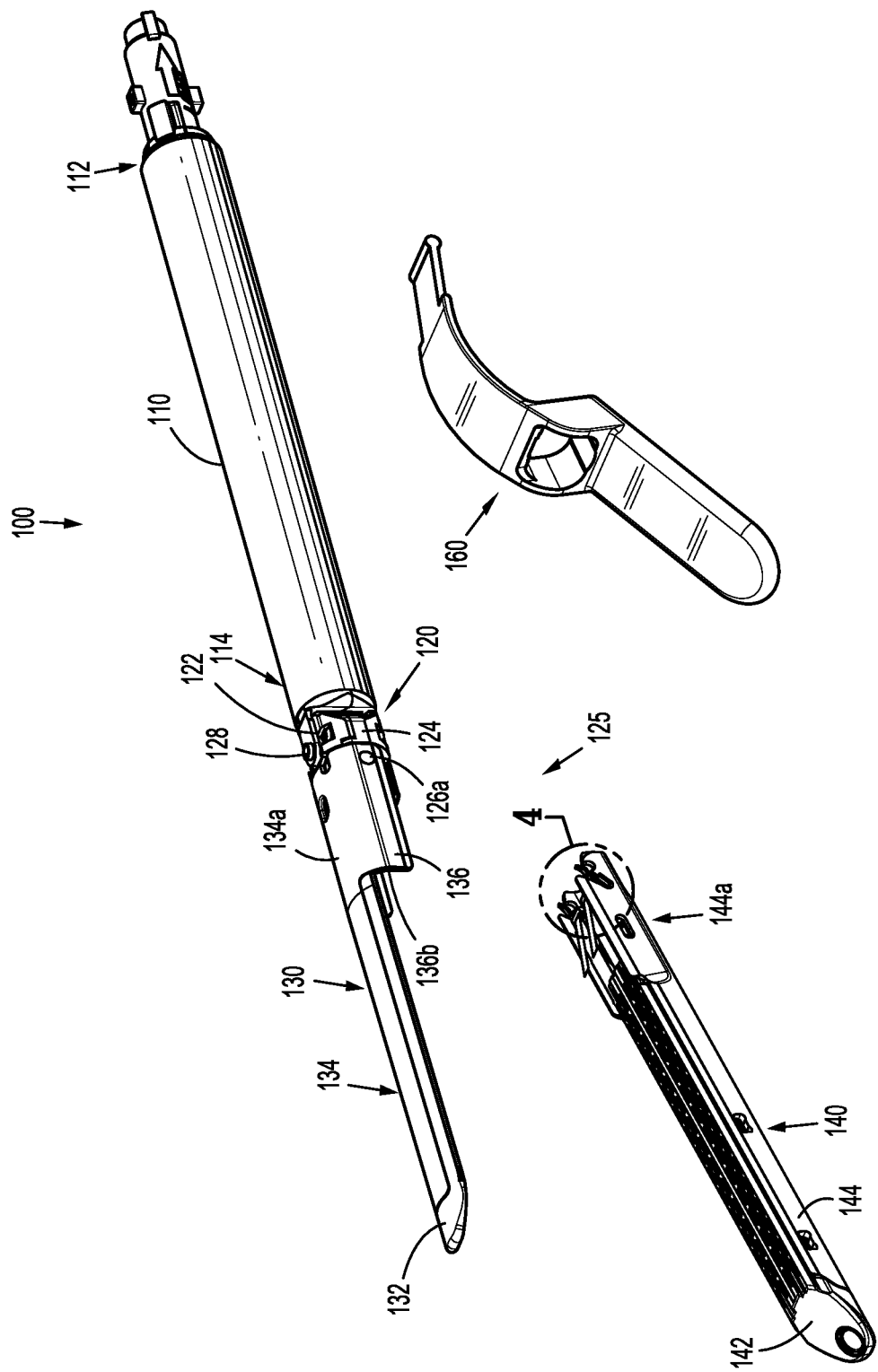
FIG. 2 is a perspective partially exploded view of the loading unit of FIG. 1 and a removal tool according to an embodiment of the present disclosure.

With particular reference now to FIG. 2, anvil assembly 130 includes an anvil portion 132 having a plurality of staple deforming concavities (not shown) and a cover plate 144 secured to a top surface of anvil portion 142 to define a cavity (not shown) therebetween. Cover plate 134 includes a proximal end 134a including a pair of side extensions 136. Side extension 136 each include a distal surface 136b. Anvil assembly 140 is secured to upper mounting portion 122 by a pivot member 128 and to lower mounting portion 124 by pivot pins 126. For a more detailed discussion of an anvil assembly substantially similar to anvil assembly 140, please refer to the Milliman '361 patent.

With reference still to FIG. 2, cartridge assembly 140 includes a staple cartridge 142 and a carrier or frame 144. A proximal end 144a of carrier 144 is configured for selective engagement with pivot pins 126 extending from lower mounting portion 122. The cartridge 142, carrier 144, or both have a detent connection with the stapling assembly; in this embodiment, the carrier 144 has a detent connect with the mounting assembly. In other embodiments, other types of detent connections are used.

Figure 4:
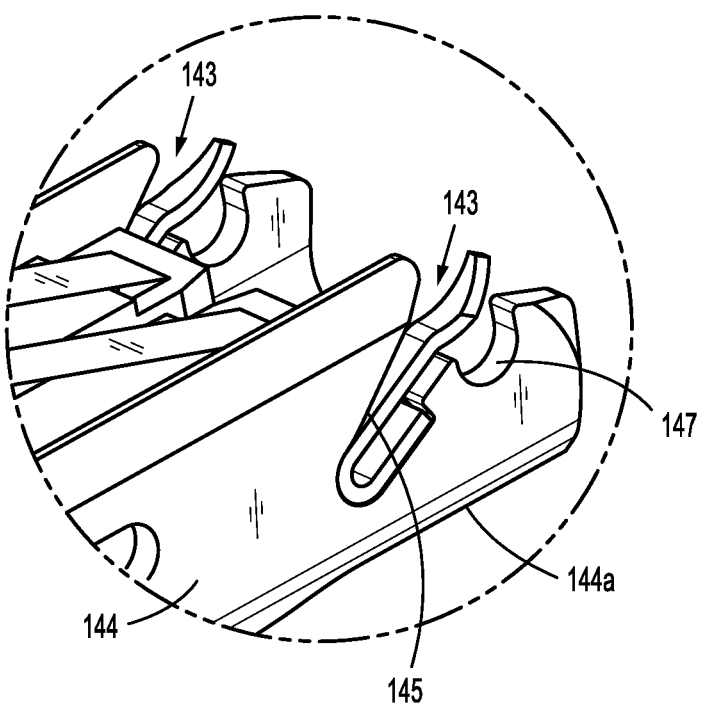
FIG. 4 is a enlarged sectional view of Section 4 of FIG. 2.
Figure 5:
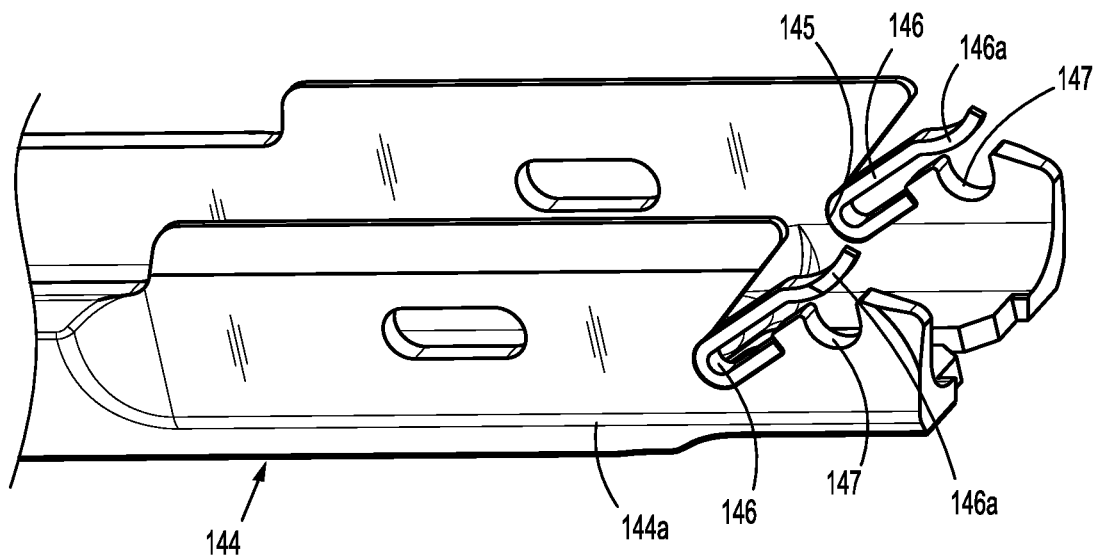
FIG. 5 is a perspective side view of a proximal end of the cartridge assembly of FIGS. 1-4.
Figure 6:
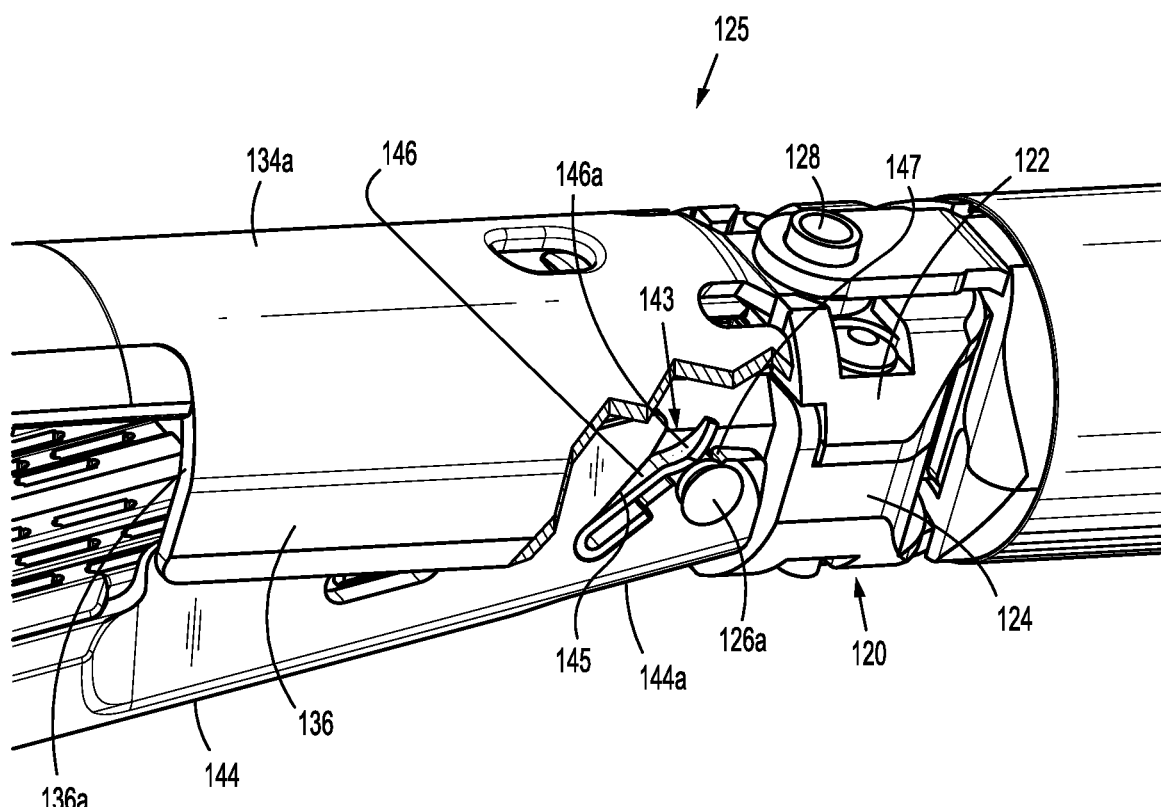
FIG. 6 is an enlarged partial cut-away perspective view of the mounting assembly of the loading unit of FIG. 1.

Turning now to FIG. 4, proximal end 144a of carrier 144 defines a pair of cut-outs 143 each including a recess 145 and a pivot hole 147 for receiving a resilient spring 146. Pivot holes 147 are each configured to at least partially receive one of pivot pins 126 extending from lower mounting portion 122. Recesses 145 are each configured to receive a spring 146. Springs 146 each define a flattened C-shaped member having a flange 146a extending therefrom. As seen in FIG. 4, springs 146 are configured to be received within recesses 145 of cut-outs 143 such that flanges 146a extend proximally and are positioned adjacent pivot holes 147. Flanges 146a operate to cover pivot holes 147. As will be discussed in further detail below, springs 146 and proximal end 144a of carrier 144 are configured such flanges 146a of springs 146 may be biased away from pivot holes 147, thereby uncovering or opening pivot holes 147 and providing access thereto.

Figure 7:
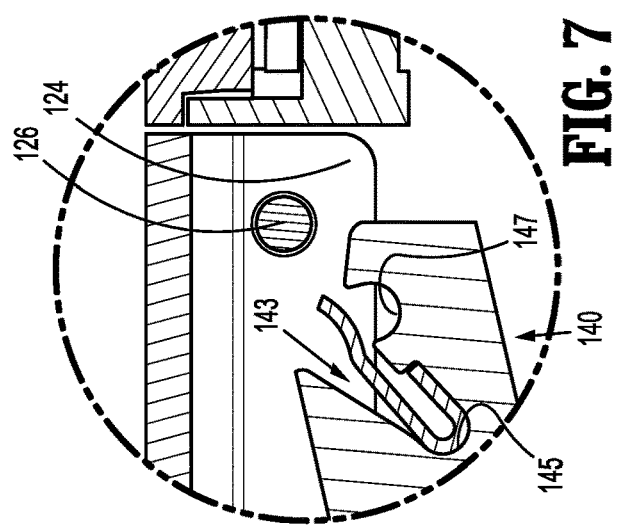
FIG. 7 is a cross-sectional side view of a mounting section of the loading unit of FIG. 1 with a replaceable staple cartridge assembly disengaged from the loading unit.

The attachment of cartridge assembly 140 to loading unit 100 will now be described with reference to FIGS. 7-9. Referring initially to FIG. 7, cartridge assembly 140 is positioned adjacent lower mounting portion 124 such that cut-outs 143 formed in proximal end 144a of carrier 144 are aligned with pivot pins 126 extending from lower mounting portion 124.

Figure 8:
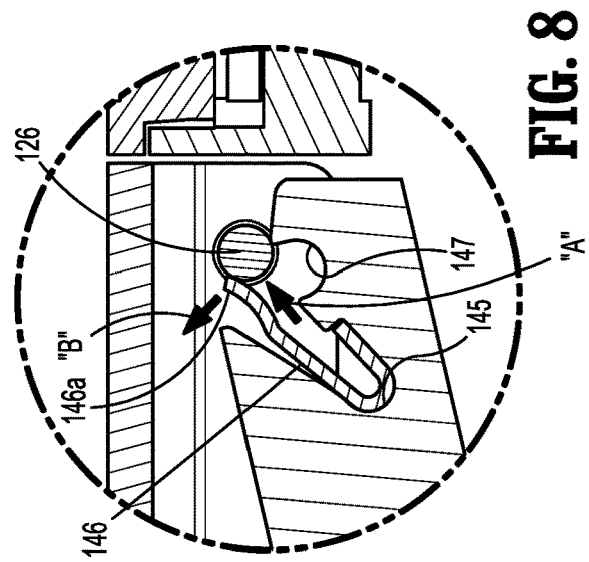
FIG. 8 is a cross-sectional side view of the mounting section of FIG. 7 with the replaceable cartridge assembly partially engaged with the loading unit.

Turning to FIG. 8, cartridge assembly 140 is then approximated towards lower mounting portion 124, as indicated by arrow "A", such that flanges 146a of springs 146 engage pivot pins 126. Continued advancement of cartridge assembly 140 towards lower mounting portion 124 causes flanges 146a of springs 146 to bias away from pivot holes 147, as indicated by arrow "B". Once flanges 146a are sufficiently biased away from pivot holes 147, pivot holes 147 are uncovered or open, thereby permitting reception of pivot pins 126 therein.

Figure 9:
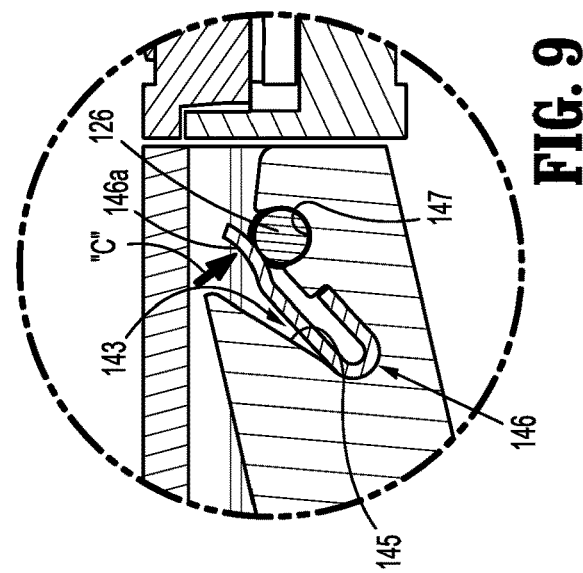
FIG. 9 is a cross-sectional side view of the mounting section of FIG. 7 with the reloadable staple cartridge assembly fully engaged with the loading unit.

With reference to FIG. 9, the reception of pivot pins 126 within pivot holes 147 releases the force on flanges 146a of spring 146, thereby allowing flanges 146a to return to an unbiased position, as indicated by arrow "C". In this manner, flanges 146a of springs 146 capture pivot pins 126 within pivot holes 147, thereby securing cartridge assembly 140 to loading unit 100. In one embodiment, an audible sound is made as pivot pins 126 are snapped into place, thereby providing a user with indication that cartridge assembly 140 is properly secured to lower mounting support 124 of loading unit 100.

Figure 10:
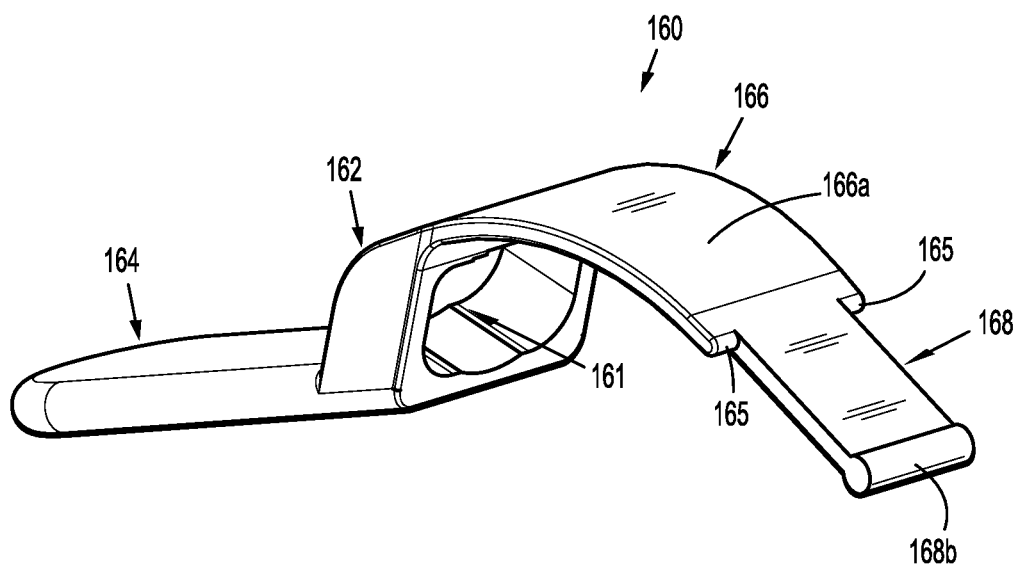
FIG. 10 is perspective view of the removal tool of FIG. 2.

With reference to FIG. 10, a tool for separating cartridge assembly 140 from elongated body portion 110 is shown generally as removal tool 160. Removal device 160 includes a base portion 162, a handle portion 164 extending from base portion 162, an arcuate portion 166 extending opposite handle portion 164 and an engagement portion 168 extending from arcuate portion 166. Base portion 162 defines an opening 161 configured to receive a distal end 140b of cartridge assembly 140 therethrough. As will be discussed in further detail below, opening 161 is configured to receive cartridge assembly 140. Base portion 162 grips cartridge assembly 140 after reception of cartridge assembly 140 through opening 161 and upon pivoting of cartridge assembly 140 relative to cartridge or base portion 142. Handle portion 164 is configured for operable engagement by a user.

With reference still to FIG. 10, arcuate portion 166 of removal device 160 defines a curve and includes an outer surface 166a. As will be discussed in further detail below, arcuate portion 166 engages anvil assembly anvil portion 134 of anvil assembly 130 to facilitate separation of cartridge assembly 140 from pivot pins 126 extending from lower mounting member 124 of mounting assembly 120. A distal end 168b of engagement portion 168 of removal tool 160 is configured to be received between side extensions 136 formed in proximal end 134a of anvil cover 134 of anvil assembly 130 and to engage staple cartridge 144 of staple assembly 140 when distal end 140b of cartridge assembly 140 is received through opening 161 formed in base portion 162. As shown, distal end 168b of engagement portion 168 is rounded; however distal end 168b may include any configuration suitable for engaging staple cartridge 144. The transition between arcuate portion 166 and engagement portion 140 forms a pair of shoulders 165. Shoulders 165 are configured to engage distal surfaces 136a formed on proximal end 134a of cover plate 134 of anvil assembly 130 after distal end 140b of cartridge assembly 140 is received through opening 161 in base portion 162 of removal tool 160.

The use of removal tool 160 to separate cartridge assembly 140 from mounting assembly 120 of loading unit 100 will now be described with reference to FIGS. 11-18. Although the separation of cartridge assembly 140 from loading unit 100 is being described with reference to removal tool 160, it is envisioned that, in some embodiments, cartridge assembly 140 may be removed with alternative tools or without the use of a tool.

Figure 11:
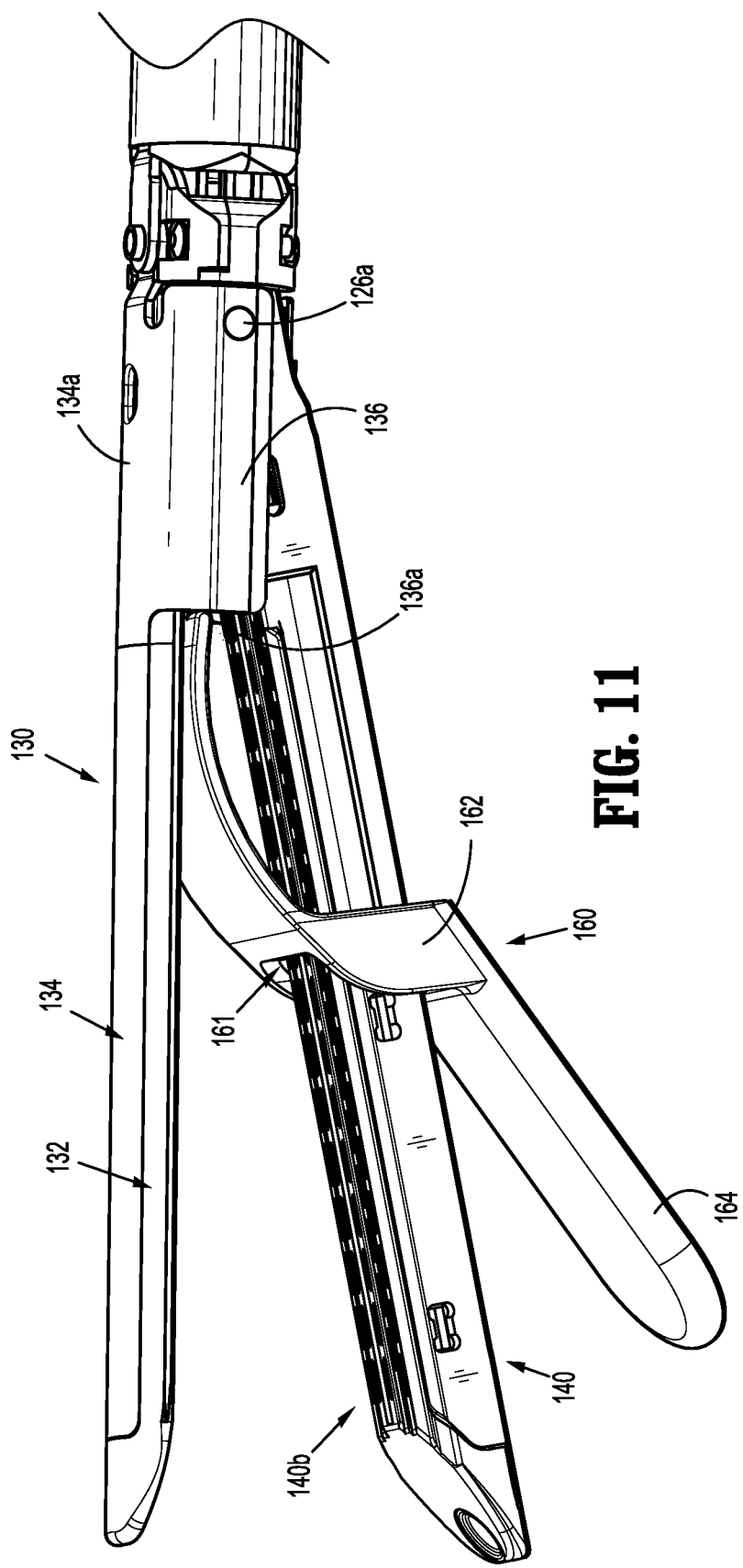
FIG. 11 is a side view of the stapling and mounting assemblies of the loading unit of FIG. 1 with the cartridge assembly engaged by the removal tool of FIG. 10.

Referring initially to FIG. 11, distal end 140b of cartridge assembly 140 is received through opening 161 of base portion 162 of removal tool 160 such that handle portion 164 is adjacent distal end 140b of cartridge assembly 140.

Figure 12:
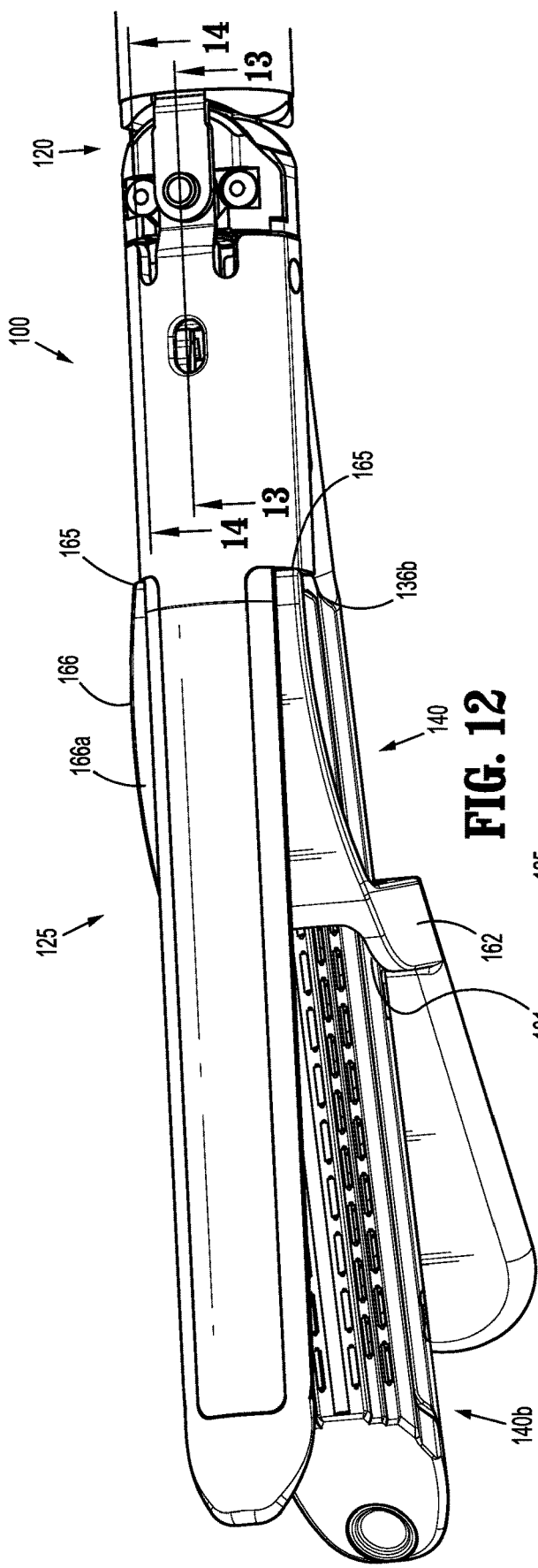
FIG. 12 is a top view of the stapling and mounting assemblies of the loading unit and the removal tool of FIG. 11.
Figure 13:
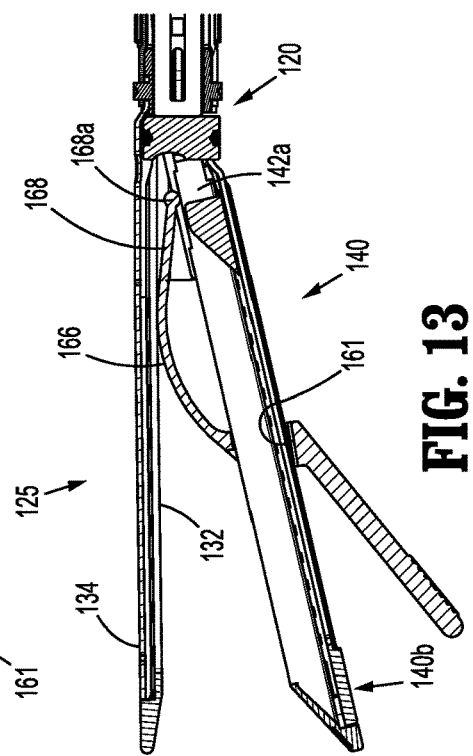
FIG. 13 is a cross-sectional side view of the stapling and mounting assemblies of FIG. 12 taken along line 13-13 of FIG. 12.

Turning briefly to FIGS. 12 and 13, distal end 140b of cartridge assembly 140 is received through opening 161 formed in base portion 162 of removal tool 160 until shoulders 165 formed between arcuate portion 166 and engagement portion 168 engage distal surfaces 136a of side extensions 136 formed on cover plate 134 of anvil assembly 130. In this position, and as shown, distal end 168a of engagement portion 168 engages proximal end 142a of staple cartridge 142 of cartridge assembly 140 while outer surface 166a of arcuate portion 166 engages anvil portion 132 of anvil assembly 130.

With reference now to FIGS. 14 and 15, prior to providing any force to removal tool 160, springs 146 mounted in cut-outs 143 in proximal ends 144 of carrier 144 of cartridge assembly 140 secure carrier 144 to mounting assembly 120 of loading unit 100. More particularly, and as discussed above, flanges 146a of springs 146 capture pivot pins 126 of mounting assembly 120 within pivot holes 147 formed in carrier 144.

Turning now to FIGS. 16 and 17, applying a force to handle portion 164 of removal tool 160 in the direction of cartridge assembly 140, as indicated by arrow "D", causes cartridge assembly 140 to grip base portion 162 of removal tool 160 as cartridge assembly 140 is pivoted within opening 161. The gripping of cartridge assembly 140 by base portion 162 causes a fulcrum or pivot point. Continued force on handle portion 164 also creates a pushing force through shoulders 165 against distal surface 136a of side extensions 136 formed on proximal end 134a of cover portion 134 of anvil assembly 130, as indicated by arrow "E". With sufficient force applied to handle portion 164, removal tool 160 overcomes the spring force provided by springs 146 thereby causing pivot pins 126 to escape from within pivot holes 147, as indicated by arrow "F".

Figure 18:
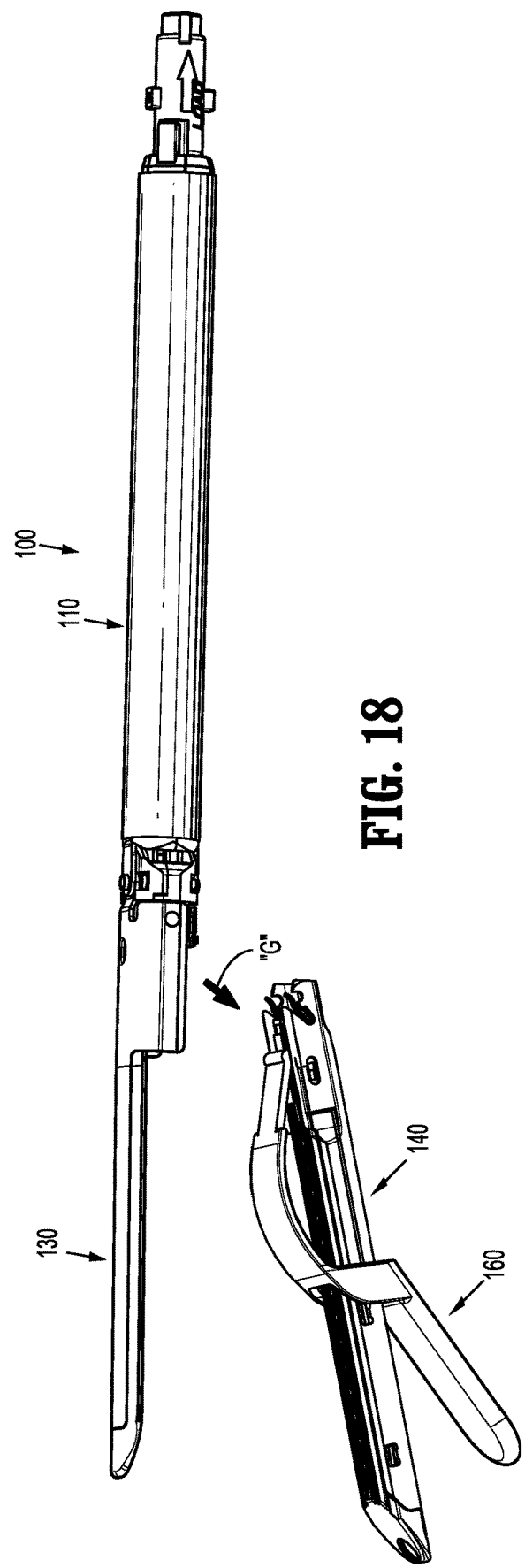
FIG. 18 is a side view of the loading unit and the removal tool of FIG. 12 with the cartridge assembly completely disengaged from the loading unit.

With reference now to FIG. 18, separation of cartridge assembly 140 from mounting assembly 120, as indicated by arrow "G", is achieved when pivot pins 126 are completely free of pivot holes 147. An audible sound is made as flanges 146a of springs 146 snap back into place after cartridge assembly 140 is separated from loading unit 100. In this manner, a user receives audible confirmation that cartridge assembly 140 has been fully disengaged from loading unit 100. Cartridge assembly 140 may then be removed from within opening 161 of base portion 162 of removal tool 160. Removal tool 160 may be disposed of or reused as desired.

Figure 19:
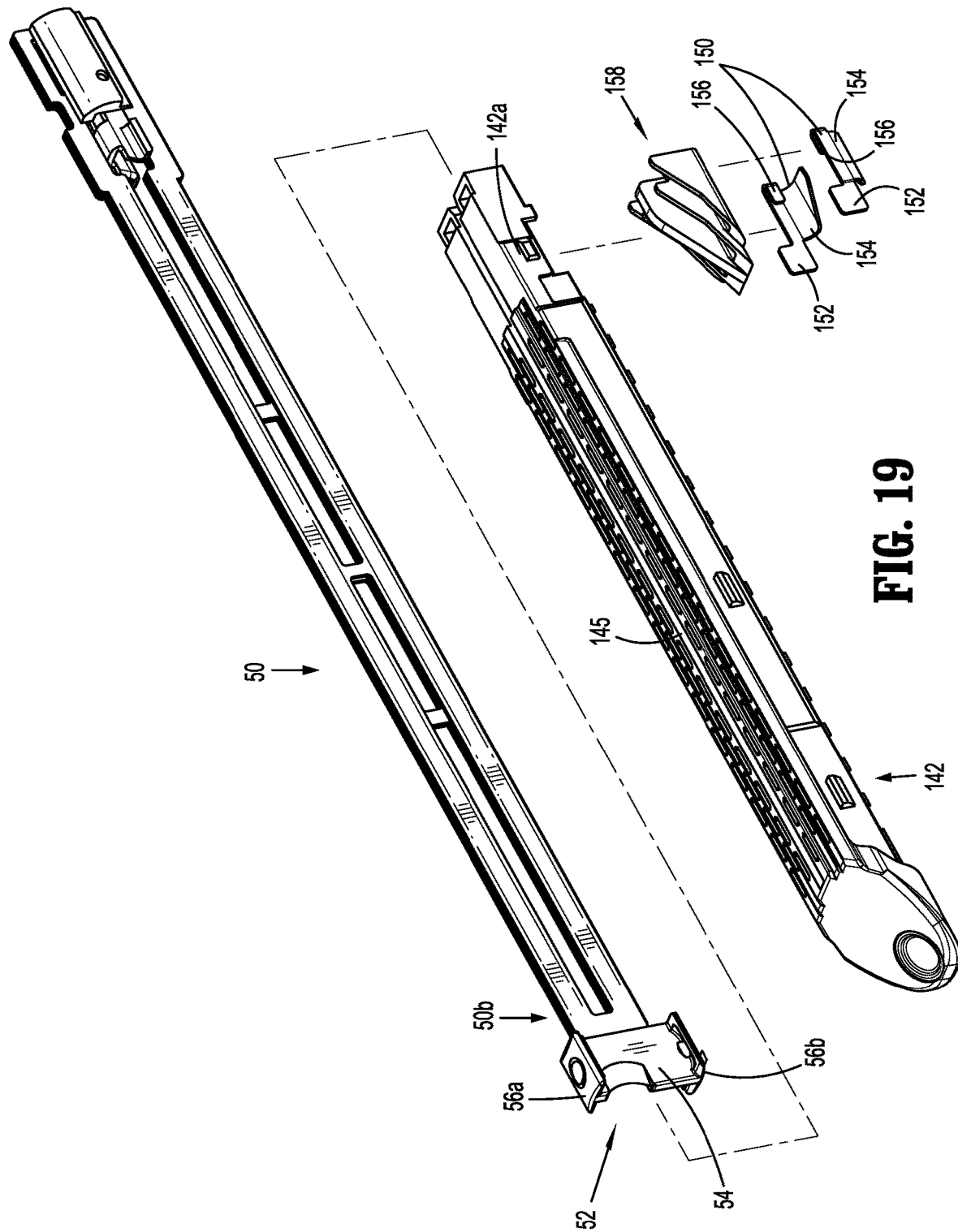
FIG. 19 is an enlarged exploded view of a drive member and staple cartridge of the loading unit of FIG. 2 and a drive member for actuating the staple assembly of FIG. 12.
Figure 20:
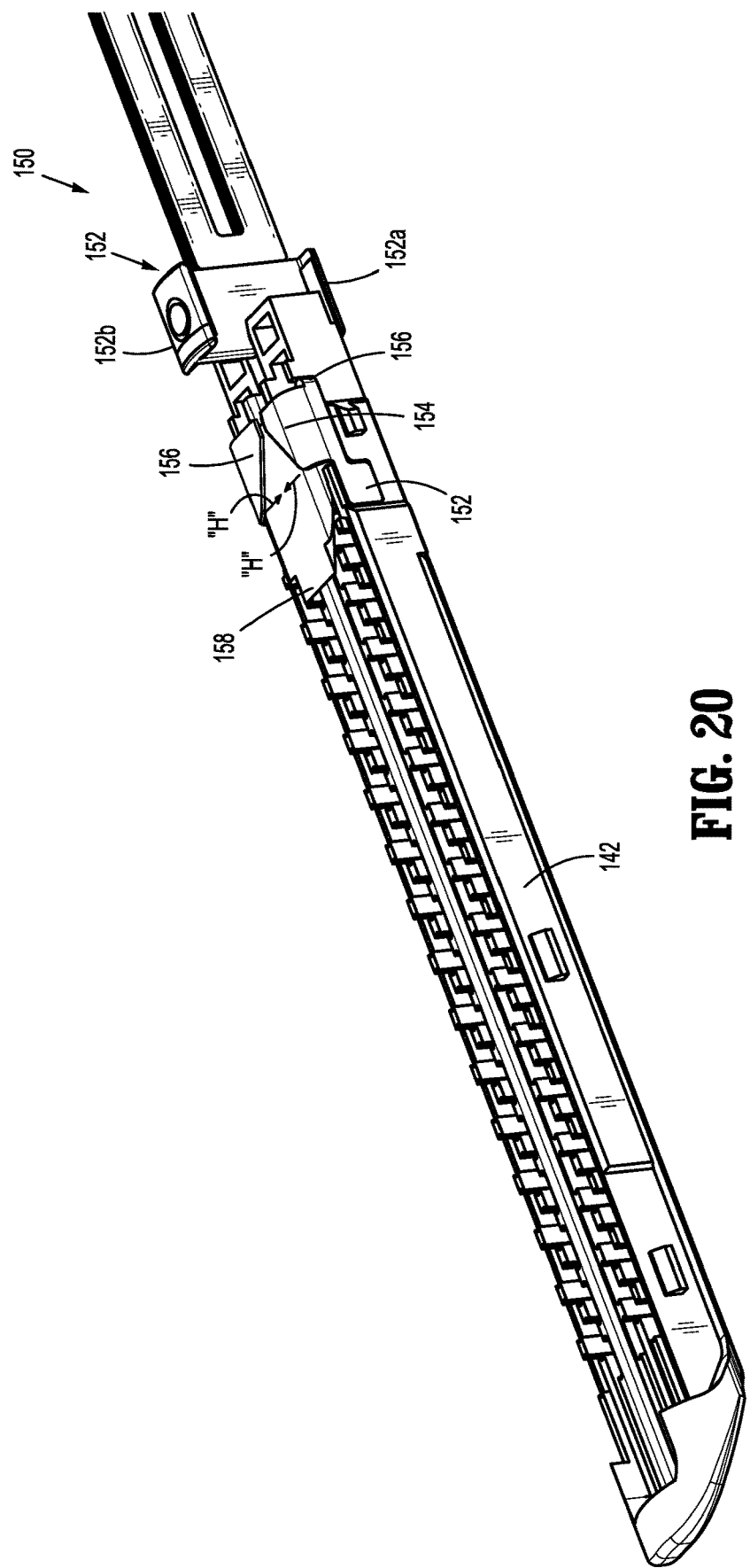
FIG. 20 is a bottom perspective view of the staple cartridge and knife assembly of the drive member of FIG. 19 with the knife assembly partially engaged with the staple cartridge.

With reference now to FIGS. 19 and 20, loading unit 100 (FIG. 2) includes a flexible drive member 50 configured to actuate staple formation in stapling assembly 125. Flexible drive member 50 includes a knife assembly 52 mounted on a distal end 50b thereof. Knife assembly 52 includes a base portion 54 and upper and lower flange members 56a, 56b. Base portion 54 may include a knife or blade 54a for cutting tissue. Upper flange member 56a is configured to be received within the space (not shown) formed between anvil portion 132 and cover portion 134 of anvil assembly 130 (FIG. 2). Lower flange member 56b is configured to be received within a space (not shown) between staple cartridge 142 and carrier 144 of cartridge assembly 140.

With continued reference to FIGS. 19 and 20, staple cartridge 142 of cartridge assembly 140 defines a longitudinal slot 145 configured for receipt of base portion 54 of flexible drive member 50. Mounted on proximal end 142a of staple cartridge 142 is a pair of interlocking plates or members 150. Interlocking plates 150 include a first L-shaped surface 152, interlocking portions 154 and pivot portions 156. Interlocking plates 150 are mounted on either side of staple cartridge 142 on a bottom surface thereof. Interlocking plates 150 are biased inwardly by pivot portions 156 towards longitudinal slot 145, as indicated by arrows "H". When loading unit 100 is in a first, unfired condition, a sled 158 for driving staple pushers (not shown) maintains interlocking plates 150 separate from each other.

The operation of interlocking plates 150 will now be described with reference to FIGS. 21-25. Referring initially to FIG. 21, in the first or unfired condition, knife assembly 52 of flexible drive member 50 is positioned proximal of proximal end 142a of staple cartridge 142 of cartridge assembly 140.

With reference now to FIG. 22, advancement of flexible drive member 50, in the direction indicated by arrow "I" (the distal direction), causes knife assembly 52 to be received within longitudinal slot 145 of staple cartridge 142 and to engage sled 158. Turning now to FIG. 23, continued advancement of flexible drive member 50, as indicated by arrow "J", causes advancement of sled 158. Movement of sled 158 from between interlocking plates 150 causes interlocking plates 150 to bias towards one another, as indicated by arrows "K". The presence of flexible drive member 50 between interlocking plates 150 prevents interlocking plates 150 from overlapping.

Turning now to FIG. 24, upon completion of the firing stroke, flexible drive assembly 50 is retracted through longitudinal slot 145 of staple cartridge 142, as indicated by arrow "L". As flexible drive assembly 50 is retracted, base 54 (FIG. 19) of knife assembly 52 passes between interlocking portions 156 of interlocking plates 150. A chamfered proximal edge (not shown) of base 54 of knife assembly 52 deflects interlocking plates 150 away from one another to permit the passage of knife assembly 52 therebetween.

With reference now to FIG. 25, once knife assembly 52 of flexible drive assembly 50 has completely passed through interlocking plates 150, interlocking plates 150 are biased towards one another, as indicated by arrows "M". Interlocking portions 156 of interlocking plates 150 are configured to prevent refiring of surgical stapling device 10 (FIG. 1). More particularly, proximal ends 156a of interlocking portions 156 overlap to prevent knife assembly 52 of flexible drive assembly 50 from readvancing through longitudinal slot 145 of staple cartridge 142.

Once flexible drive assembly 50 is completely retracted from within longitudinal slot 145 and disengaged from staple cartridge 142, cartridge assembly 140 may be separated from mounting assembly 120 of loading unit 100 in the manner discussed above. A second cartridge assembly may then be secured to mounting portion 120 of loading unit 100 as discussed above.

Figure 26:
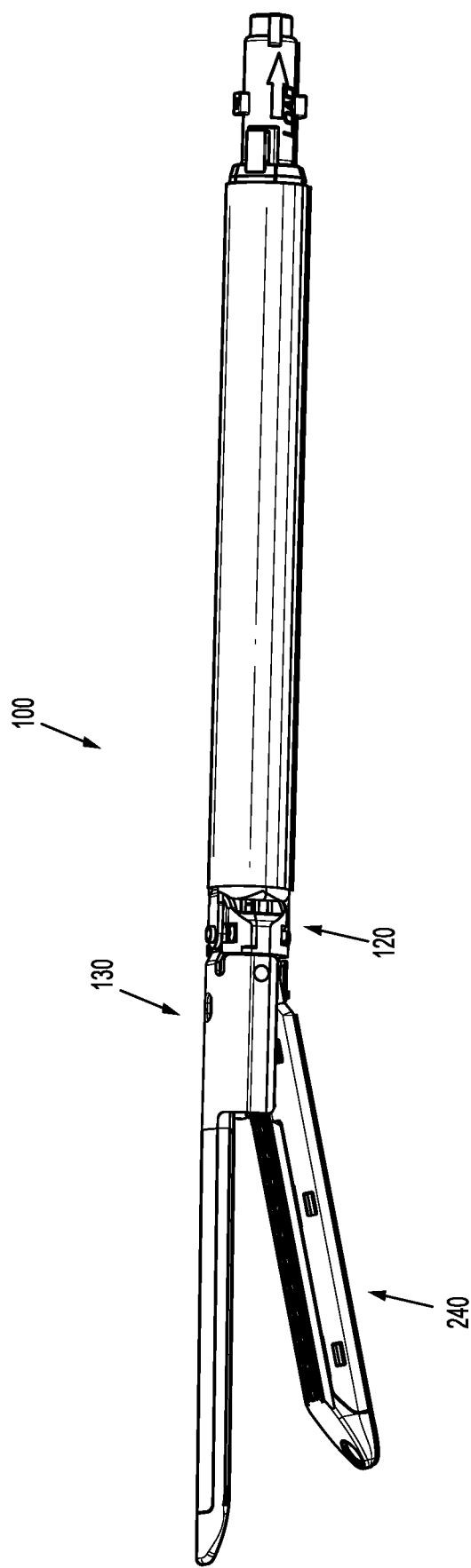
FIG. 26 is a side view of a loading unit including an alternative embodiment of a cartridge assembly according to the present disclosure.

With reference now to FIG. 26, mounting assembly 120 and anvil assembly 130 are configured such that a cartridge assembly of the same diameter and the same or shorter lengths may be operably secured to loading unit 100. For example, in one embodiment, a loading unit including an anvil assembly having a 12 mm diameter and a 60 mm length may receive a reloadable cartridge assembly having a diameter of 12 mm and a length of 60 mm or less. In this manner, and as shown in FIG. 26, a cartridge assembly 240 having a length shorter than cartridge assembly 140 may be secured to mounting assembly 120 of loading unit 100. In one embodiment, anvil assembly 130 measures 60 mm in length and cartridge assembly 240 measures 45 mm in length.

Loading unit 100 may be provided with one or more cartridge assemblies. The cartridge assemblies may be of same or differing sizes. In one embodiment, loading unit 100 is provided to a surgeon preassembled, i.e., with a replaceable cartridge assembly secured thereto. Alternatively, one or more cartridge assemblies are provided separate of loading unit 100. Since the anvil assembly must be at least as long as the cartridge assembly for the loading unit to function properly, an anvil assembly provided with the loading unit should include a length at least equal to the longest cartridge assembly provided for use with the loading unit.

Figure 27:
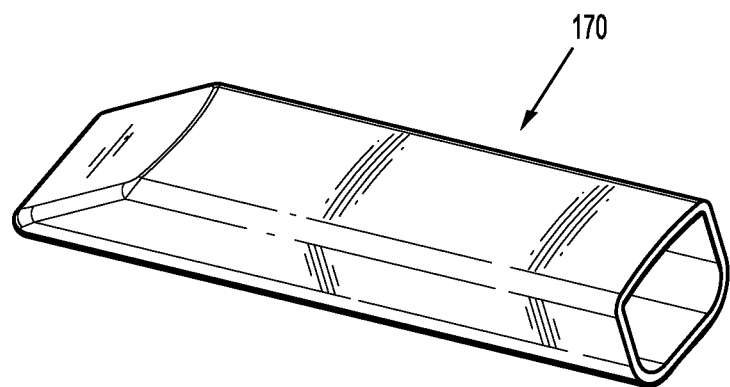
FIG. 27 is a perspective view of a protective sleeve for use with the cartridge assemblies of the present disclosure.
Figure 28:
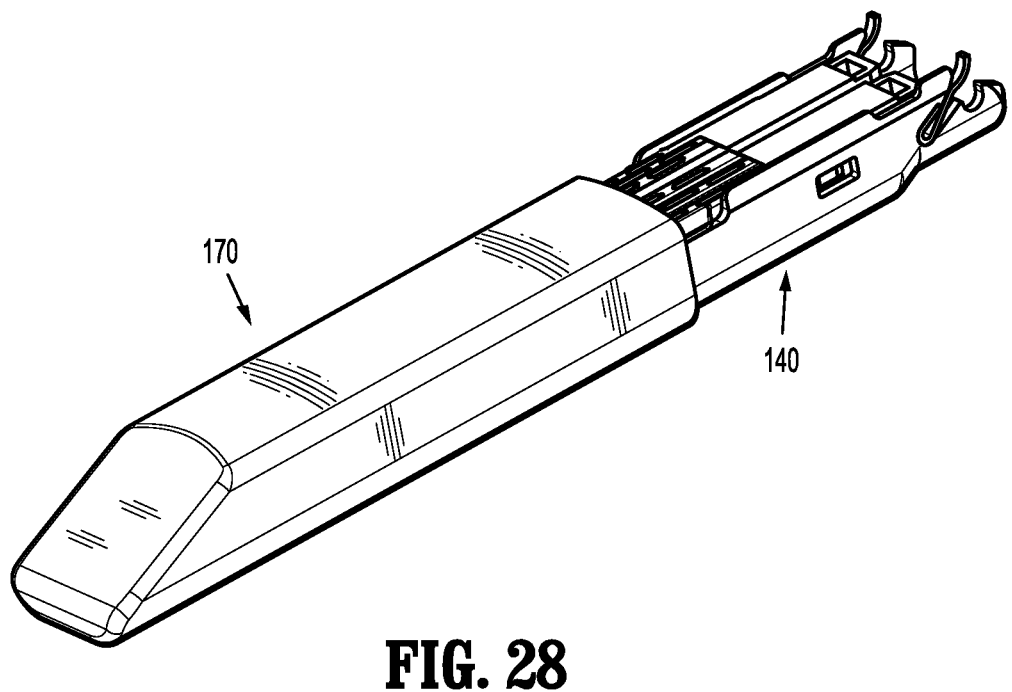
FIG. 28 is perspective view of the protective sleeve of FIG. 27 in use with a cartridge assembly of the present disclosure.

With reference now to FIGS. 27 and 28, cartridge assembly 140 may be provided with a protective sleeve 170. Protective sleeve 170 is configured to receive a distal end 140b of cartridge assembly 140 and extend along the length of staple cartridge 142. Protective sleeve 170 may protect cartridge assembly 140 from damage during shipment and/or installation. Protective sleeve 170 may additionally assist in retaining staples (not shown) within staple cartridge 142.

It will be understood that various modifications may be made to the embodiments disclosed herein. For example, the staple cartridge may include alternative configurations, including a dissecting tip extending from a distal end thereof. Therefore, the above description should not be construed as limiting, but merely as exemplifications of particular embodiments. Those skilled in the art will envision other modifications within the scope and spirit of the claims appended hereto.

The invention claimed is:

1. A surgical stapling device comprising:
an elongate body having proximal and distal portions and defining a longitudinal axis; and
a stapling assembly disposed on the distal portion of the elongate body, the stapling assembly having a mounting assembly, and first and second jaws secured to the mounting assembly, the first jaw including an anvil assembly, and the second jaw including an elongate channel and a staple cartridge received within the elongate channel, wherein the elongate channel is pivotally and releasably secured to the mounting assembly to permit replacement of the second jaw by a user during a surgical procedure.

2. The surgical stapling device of claim 1, wherein the elongate channel includes proximal and distal portions, the proximal portion of the elongate channel defines a pair of cut-outs.

3. The surgical stapling device of claim 2, wherein each cut-out includes a recess and a pivot hole.

4. The surgical stapling device of claim 3, wherein each recess is configured to receive a spring.

5. The surgical stapling device of claim 4, wherein each pivot hole is configured to receive a pivot pin.

6. The surgical stapling device of claim 5, wherein each spring includes a flange for selectively retaining the pivot pin within each of the pivot holes.

7. The surgical stapling device of claim 1, wherein the stapling assembly is pivotable relative to the elongate body.

8. The surgical stapling device of claim 1, further including an actuation assembly in operable connection with the elongate body.

9. The surgical stapling device of claim 8, wherein the elongate body is rotatable about the longitudinal axis.

10. The surgical stapling device of claim 1, wherein the elongate body and the stapling assembly form a loading unit.

11. The surgical stapling device of claim 1, wherein the stapling assembly is movable between a non-articulated position along the longitudinal axis of the elongate body and an articulated position relative to the longitudinal axis of the elongate body.

12. A surgical stapling device comprising:
an elongate body having proximal and distal portions and defining a longitudinal axis; and
a stapling assembly disposed on the distal portion of the elongate body, the stapling assembly having a mounting assembly, and first and second jaws secured to the mounting assembly, wherein the second jaw is pivotally and releasably secured to the mounting assembly to permit replacement of the second jaw by a user during a surgical procedure.

13. The surgical stapling device of claim 12, wherein the first jaw includes an anvil assembly and the second jaw includes an elongate channel and a staple cartridge received within the elongate channel.

14. The surgical stapling device of claim 13, wherein the elongate channel is pivotally and releasably secured to the mounting assembly.

15. The surgical stapling device of claim 13, wherein the elongate channel includes proximal and distal portions, the proximal portion of the elongate channel defines a pair of cut-outs.

16. The surgical stapling device of claim 15, wherein each cut-out includes a recess and a pivot hole.

17. The surgical stapling device of claim 16, wherein each recess is configured to receive a spring and each pivot hole is configured to receive a pivot pin.

18. The surgical stapling device of claim 17, wherein each spring includes a flange for selectively retaining the pivot pin within each of the pivot holes.

19. The surgical stapling device of claim 12, further including an actuation assembly in operable connection with the elongate body.

20. A surgical stapling device comprising:
an elongate body having proximal and distal portions and defining a longitudinal axis; and
a stapling assembly disposed on the distal portion of the elongate body, the stapling assembly having a mounting assembly, and first and second jaws secured to the mounting assembly, the first jaw including an anvil assembly, and the second jaw including an elongate channel and a staple cartridge received within the elongate channel, the elongate channel includes proximal and distal portions, the proximal portion of the elongate channel defines a pair of cut-outs, each cut-out including a recess and a pivot hole, wherein the elongate channel is pivotally and releasably secured to the mounting assembly.

* * * * *